United States Patent [19] [11] 4,374,293
Burrington et al. [45] Feb. 15, 1983

[54] INDENE PRODUCTION FROM AROMATIC OLEFINS

[75] Inventors: J. D. Burrington, Richmond Heights; R. K. Grasselli, Chagrin Falls; C. T. Kartisek, Sagamore Hills, all of Ohio

[73] Assignee: The Standard Oil Co., Cleveland, Ohio

[21] Appl. No.: 293,030

[22] Filed: Aug. 14, 1981

[51] Int. Cl.³ ............................................. C07C 12/64
[52] U.S. Cl. .................. 585/410; 260/465 D; 260/465 F; 260/465 G; 260/465 R; 560/20; 560/23; 560/51; 560/53; 560/64; 560/65; 562/434; 562/438; 562/439; 562/463; 562/466; 568/424; 568/440; 568/441; 568/585; 568/632; 568/705; 568/706; 568/734; 568/929; 570/127; 570/148; 570/183; 585/361
[58] Field of Search .................. 585/410, 361; 260/465 D, 465 F, 465 G, 465 R; 560/20, 23, 51, 53, 64, 65; 562/434, 438, 459, 463, 466; 568/424, 440, 441, 585, 632, 705, 706, 734, 729; 570/127, 148, 183

[56] References Cited

U.S. PATENT DOCUMENTS 3,452,032 6/1969 Grasselli et al. ..................... 546/340
4,049,727 9/1977 Gelfand ........................... 570/183 X

FOREIGN PATENT DOCUMENTS 3101352 2/1977 Japan .................................. 568/441
5013207 7/1978 Japan .................................. 568/734
406820 8/1971 U.S.S.R. ............................... 585/410
703519 3/1978 U.S.S.R. ............................... 585/469

OTHER PUBLICATIONS

Chemical Abstract, 75: P63494h, (Czech. 137,475).
Chemical Abstract 51: P5403, (U.S. 2,775,629).
Chemical Abstract 28: P2373, 28; P2732.

Primary Examiner—Delbert E. Gantz
Assistant Examiner—A. Pal
Attorney, Agent, or Firm—John E. Miller, Jr.; Herbert D. Knudsen; Larry W. Evans

[57] ABSTRACT

Allylbenzene is converted to indene by means of a tungsten-containing catalyst.

15 Claims, No Drawings

INDENE PRODUCTION FROM AROMATIC OLEFINS

BACKGROUND AND SUMMARY OF THE INVENTION

The present invention relates to a novel technique for forming indene from allylbenzene.

U.S. Pat. No. 3,452,032 describes a process for producing cinnamaldehyde wherein allylbenzene and oxygen are contacted with certain metal oxide complexes known to function as oxidation and ammoxidation catalysts. In accordance with the present invention, it has now been discovered that indene can be produced in this reaction in significant amounts if the oxide complex catalyst contains tungsten in significant amounts.

Accordingly, the present invention provides a novel process for producing indene from allylbenzene wherein allylbenzene and oxygen are contacted with an oxide or an oxide complex catalyst containing at least 30 atom % tungsten, the percent being based on the metal atoms in the complex excluding oxygen.

More specifically, the present invention provides a process for producing indene from allylbenzene where allylbenzene and oxygen are contacted with a phosphorous and molybdenum-free oxide or oxide complex catalyst of the following formula:

$$A_a B_b C_c WO_x$$

wherein

A is at least one element selected from the group consisting of periods IA, IIA of the Periodic Table and Tl, B is at least one element selected from the group consisting of Cu, Co, Fe, Mn, Cr and Ce, and C is at least one element selected from the group consisting of Bi, Sb, U, V and Sn, and further wherein a equals 0 to 10, b equals 0 to 10, c equals 0 to 10, and x is a number sufficient to satisfy the valence requirements of the other elements present.

DETAILED DESCRIPTION

Catalyst

The catalysts useful in the invention are oxides and oxide complexes containing at least 30 atom % tungsten based on the metal atoms in the oxide complex other than oxygen.

Preferred catalysts are oxides and oxide complexes of tungsten which are free of phosphorus and molybdenum. Such materials can be defined by the formula $$A_a B_b C_c WO_x$$

wherein

A is at least one element selected from Groups IA and IIA of the Periodic Table and Tl, B is at least one element selected from the group consisting of Cu, Co, Fe, Ni, Mn, Cr and Ce, and C is at least one element selected from the group consisting of Bi, Sb, U, V and Sn, and further wherein a equals 0 to 10, b equals 0 to 10, c equals 0 to 10, and x is a number sufficient to satisfy the valence requirements of the other elements present.

Of the above catalysts, a preferred group are those which are free of antimony and further in which any silicon present is not complexed with tungsten in the form of a heteropolyanion.

Of these and even a more preferred group are those in which a is 0 to 1, b is 0 to 1 and c is 0 to 1.

Still more preferred are those of the above catalysts in which $0 < a + b + c \leq 1$.

A particularly preferred class of catalysts are those which contain bismuth and at least one basic metal, i.e. a metal selected from Group IA and/or Group IIA of the Periodic Table and Tl, especially potassium, cesium, barium and magnesium. As well known in catalysis, an appropriate balance must be struck between the various ingredients in a specific composition in order that good catalytic properties are obtained. This is also true in the present invention and is illustrated by the following Examples 13 in which the conversion is too low because the catalyst contains too much basic metal.

The catalysts of the invention can be prepared in a conventional manner and can be used unsupported or supported on a suitable catalyst support. Catalyst supports useful in various oxidation reaction are well known in the art and any such support material can be used. Silica, alumina, titania and Alundum (alumina/silica) are preferred.

Reactants

The present invention finds primary use in connection with the conversion of allylbenzene to indene. However, substituted allylbenzenes can also be employed. Such compounds can be illustrated by the formula

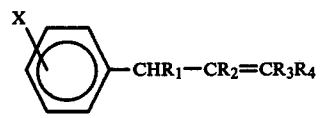

wherein X is F, Br, I, Cl and/or $OR_5$ wherein $R_5$ is H or $C_{1-4}$ alkyl, and wherein each of $R_1$, $R_2$, $R_3$ and $R_4$ are independently F, Cl, Br, I, $OR_6$, $CO_2R_6$, CHO, CN, $NO_2$, H, $C_{1-14}$ alkyl, or $C_{6-14}$ aryl, wherein $R_6$ is H, $C_{1-14}$ alkyl or $C_{6-14}$ aryl.

Reaction Conditions

The inventive process is carried out using the same reaction conditions as employed in U.S. Pat. No. 3,452,032, the disclosure of which is incorporated herein by reference. Preferably, however, the reaction temperature is below 350° C. with a reaction temperature of 300° to 345° C., more preferably 310° to 330° C. being especially preferred. In addition, the contact time is preferably about 0.05 to 10 seconds, even more preferably 0.3 to 1.2 seconds. Furthermore, the reaction system is also preferably free of water and in addition the catalyst is preferably used unsupported.

WORKING EXAMPLES

A number of oxides and oxide complexes in accordance with the present invention as well as a few representatives of the prior art were used to oxidize allylbenzene to indene. The catalysts were prepared by conventional methods, which involved dissolving the metal nitrates of barium, calcium, magnesium, potassium, cesium, iron in water. The appropriate solutions were then added to an aqueous solution of ammonium metatungstate with or without a 40% silica sol. Bismuth-containing catalysts were prepared by dissolving bismuth nitrate in 10% $HNO_3$ and adding to an aqueous solution of the remaining components of the catalyst preparation. The resulting slurries were evaporated on a hot plate and dried in an oven at 120° C. for 16 hours. They were then heated at 290° C. for 3 hours, 325° C. for 3 hours and 500° C. for 3 hours. The antimony oxide catalyst of Comparative Example C was further heated at 750° C. for 3 hours.

In each example, 2.5 cc catalyst was placed in a microreactor and contacted with a feed comprising allylbenzene, air, nitrogen and in some instances water. When water was present, the feed ratios were 1.0 allylbenzene/4.0 $H_2O$/11.9 air/58.1 $N_2$. Where water was absent the feed ratios were 1.0 allylbenzene/11.9 air/62.1 $N_2$. Unless otherwise indicated, the contact time in all experiments was 1.0 second and the reaction temperature was 320° C.

The gross reaction products were recovered and analyzed in a conventional manner. Catalyst identity, allylbenzene conversion, selectivity to indene, the yields of indene and cinnamaldehyde (normalized to 100% carbon balance) and the carbon balance are set-forth in the following table.

dane, the ethylenically saturated analog of indene, is produced in large amounts. Indene and indane are very difficult to separate and thus the inventive process which produces essentially no by-product indane is especially advantageous.

We claim:

1. A process for making indene or substituted indene comprising contacting a reactant of the formula $$X\text{—C}_6H_4\text{—}CHR_1\text{—}CR_2\text{=}CR_3R_4$$

wherein X is F, Br, I, Cl, H, $C_{1-14}$ alkyl, or $C_{6-14}$ aryl and/or $OR_5$ wherein $R_5$ is H or $C_{1-4}$ alkyl, and wherein each of $R_1$, $R_2$, $R_3$ and $R_4$ are independently F, Cl, Br, I, $OR_6$, $CO_2R_6$, CHO, CN or $NO_2$ wherein $R_6$ is H, $C_{1-14}$ alkyl or $C_{6-14}$ aryl and molecular oxygen with a catalyst comprising an oxide of tungsten or an oxide complex of tungsten containing at least 30 atom % tungsten based on the metal atoms in said complex excluding oxygen.

2. The process of claim 1 wherein said reactant is allylbenzene.

3. The process of claim 2 wherein said catalyst is free of phosphorus and molybdenum and is described by the

TABLE

| | | CONVERSION OF ALLYLBENZENE TO INDENE | | | |
|---|---|---|---|---|---|
| EX. NO. | CATALYST COMPOSTION | CONVERSION | SELECTIVITY TO INDENE | INDENE YIELDS | CINNAMALDEHYDE YIELDS | CARBON BALANCE |
| A | $Bi_2O_3.MoO_3$ | 6.6 | 9.0 | 0.6 | 4.7 | 94.3 |
| B | $Bi_2O_3.MoO_3$ | 6.5 | 15.4 | 1.0 | 2.4 | 103.0 |
| C | $Sb_2O_4.5\%\ SiO_2$ | 6.7 | 6.0 | 0.4 | 2.6 | 101.9 |
| D* | $USb_{4.6}O_x$ | 83.4 | 0.0 | 0.0 | 20.3 | 86.1 |
| E** | $USb_{4.6}O_x$ | 3.6 | 38.9 | 1.4 | 2.2 | 93.0 |
| 1 | $WO_3$ | 33.2 | 41.9 | 13.9 | 0.0 | 41.0 |
| 2 | $WO_3.5\%\ SiO_2$ | 38.9 | 35.4 | 13.8 | 0.0 | 54.2 |
| 3 | $WO_3.5\%\ SiO_2$ | 63.6 | 20.8 | 13.2 | 0.7 | 74.2 |
| 4 | $WO_3.20\%\ SiO_2$ | 56.7 | 25.7 | 14.6 | 0.2 | 52.0 |
| 5 | $K_{0.02}WO_x.5\%\ SiO_2$ | 5.6 | 67.9 | 3.8 | 0.0 | 79.0 |
| 6*** | $K_{0.02}WO_x.5\%\ SiO_2$ | 34.4 | 41.3 | 14.2 | 5.6 | 46.5 |
| 7 | $WK_{0.10x}$ | 23.9 | 27.6 | 6.6 | 0.7 | 101.9 |
| 8 | $WCs_{0.01}O_x.5\%\ SiO_2$ | 14.5 | 61.4 | 8.9 | 0.3 | 66.0 |
| 9 | $WCs_{0.01}O_x.5\%\ SiO_2$ | 30.7 | 27.0 | 8.3 | 0.9 | 87.0 |
| 10 | $WCs_{0.1}O_x$ | 37.3 | 22.5 | 8.4 | 0.6 | 93.1 |
| 11 | $WMg_{0.2}O_x.5\%\ SiO_2$ | 47.7 | 27.9 | 13.3 | 0.4 | 72.1 |
| 12 | $WMg_{0.5}K_{0.05}O_x$ | 36.4 | 22.5 | 8.2 | 0.6 | 79.2 |
| 13 | $WMgK_{0.1}O_x$ | 0.9 | 77.8 | 0.7 | 0.2 | 105.0 |
| 14 | $WCs_{0.2}O_x$ | 26.7 | 31.5 | 8.4 | 0.6 | 77.4 |
| 15 | $WBa_{0.2}O_x$ | 9.2 | 42.4 | 3.9 | 0.4 | 96.8 |
| 16 | $W_3Ba_{0.6}K_{0.05}O_x$ | 7.2 | 27.8 | 2.0 | 0.2 | 105.8 |
| 17 | $Bi_2W_3O_{12}.5\%\ SiO_2$ | 33.3 | 40.2 | 13.4 | 1.8 | 54.4 |
| 18 | $BiW_3K_{0.05}O_x$ | 9.0 | 70.0 | 6.3 | 1.3 | 95.8 |
| 19 | $Bi_4Ce_4W_{12}K_{0.1}O_x$ | 10.0 | 66.0 | 6.6 | 2.6 | 80.0 |
| 20 | $W_3Bi_2Ba_{0.6}K_{0.15}O_x$ | 9.6 | 67.7 | 6.5 | 1.5 | 102.1 |
| 21 | $Bi_2W_3K_{0.05}O_x$ | 8.7 | 65.5 | 5.7 | 1.5 | 87.8 |
| 22 | $K_{0.1}Ni_{2.5}Co_{4.5}Fe_3P_{0.5}Bi_1W_{12}O_x$ | 24.7 | 24.3 | 6.0 | 4.0 | 49.7 |
| 23 | $Bi_2W_3Ba_{0.6}O_x$ | 16.8 | 50.6 | 8.5 | 2.3 | 85.2 |
| 24 | $Fe_2W_3O_{12}5\%\ SiO_2$ | 46.7 | 6.0 | 2.8 | 0.4 | 50.8 |

*3 sec, 410° C.
**0.4 sec, 320° C.
***1.0 sec, 400° C.

In the above table, it can be seen that catalysts in accordance with the invention which contain tungsten provide indene in good yields and in most instances high selectivities. On the other hand, prior art catalyst such as bismuth molybdates and uranium antimonates provide very low yields of indene, if any.

Also, a further significant advantage of the present invention is that essentially no by-product indane is produced. In most processes for producing indene, informula $$A_aB_bC_cWO_x$$

wherein
A is at least one element selected from Groups IA and IIA of the Periodic Table and Tl, B is at least one element selected from the group consisting of Cu, Co, Fe, Ni, Mn, Cr and Ce, and
C is at least one element selected from the group consisting of Bi, Sb, U, V and Sn, and further
wherein
a equals 0 to 10,
b equals 0 to 10,
c equals 0 to 10, and
x is a number sufficient to satisfy the valence requirements of the other elements present.

4. The process of claim 3 wherein said catalyst is free of Sb and any Si present is not complexed with W in the form of a heteropolyanion.

5. The process of claim 4 wherein said catalyst is unsupported.

6. The process of claim 5 wherein
a is 0 to 1,
b is 0 to 1, and
c is 0 to 1.

7. The process of claim 6 wherein said process is carried out at a temperature of 300° to 345° C.

8. The process of claim 7 wherein $a+b+c \leqq 1$.

9. The process of claim 8 wherein $a+b+c>0$.

10. The process of claim 7 wherein $a+b+c>0$.

11. The process of claim 7 wherein said catalyst contains Bi and a basic metal selected from Groups IA and IIA of the Periodic Table and Tl.

12. The process of claim 11 wherein said basic metal is K, Cs, Mg and/or Ba.

13. The process of claim 12 wherein said process is carried out at a contact time of 0.3 to 1.2 seconds.

14. The process of claim 3 said catalyst contains Bi and a basic metal selected from Groups IA and IIA of the Periodic Table and Tl.

15. The process of claim 13 wherein said basic metal is K, Cs, Mg and/or Ba.

* * * * *